United States Patent [19]

Nelson et al.

[11] 4,322,539
[45] Mar. 30, 1982

[54] CONVERSION OF ETHERS TO THIOAMINES

[75] Inventors: Gunner E. Nelson; Michael J. Dagani, both of Baton Rouge, La.

[73] Assignee: Ethyl Corporation, Richmond, Va.

[21] Appl. No.: 253,168

[22] Filed: Apr. 13, 1981

Related U.S. Application Data

[63] Continuation-in-part of Ser. No. 51,984, Jun. 25, 1979, abandoned, which is a continuation-in-part of Ser. No. 883,660, Mar. 3, 1978, abandoned.

[51] Int. Cl.$^3$ ............................................ C07D 233/64
[52] U.S. Cl. ..................................................... 548/342
[58] Field of Search .......................................... 548/342

[56] References Cited

U.S. PATENT DOCUMENTS 3,950,333 4/1976 Durant et al. ................... 548/342 X
3,984,293 10/1976 King et al. ............................ 204/75
4,055,573 10/1977 Mendelson ........................... 548/335
4,189,592 2/1980 Halbritter ............................ 548/342

FOREIGN PATENT DOCUMENTS 1341376 12/1973 United Kingdom ................ 424/273

OTHER PUBLICATIONS

Theilheimer, Synthetic Methods of Organic Chem., QD262, T4 9:660; 11:667 and 670; 17:659; 19:670.
Daniels et al., Journ. Org. Chem., 1962, vol. 27, pp. 4710–4711.
Burwell, Chem. Rev. 54, pp. 635–636 (1954).
Jacques et al., Journ. Chem. Soc. (London), 1964, pp. 2683–2689.
Fieser et al., Organic Chem., 3rd Edition, p. 137 (1956).
Reid, Organic Chemistry of Bivalent Sulfur, vol. II, p. 17 (1960).
Patai, Chem. of the Ether Linkage, Interscience–Wiley, N. Y., pp. 22–42 (1967).
Patai, The Chemistry of the Hydroxyl Group, Part I Interscience–Wiley, N. Y. pp. 627–628 (1971).

Primary Examiner—Ethel G. Love
Attorney, Agent, or Firm—Donald L. Johnson; John F. Sieberth; Willard G. Montgomery

[57] ABSTRACT

Bis-(imidazolylmethyl)-ether hydrochloride conversion to the corresponding amino-alkylene-thiomethyl imidazoles by reaction with amino alkylene thiols.

10 Claims, No Drawings

CONVERSION OF ETHERS TO THIOAMINES

CROSS-REFERENCE TO RELATED APPLICATIONS

This application is a continuation-in-part of application Ser. No. 51,984, filed June 25, 1979, now abandoned, which in turn is a continuation-in-part of application Ser. No. 883,660, filed March 3, 1978, now abandoned.

BACKGROUND OF THE INVENTION

This invention relates to a process for preparing thioamines such as 4-(amino-alkylene-thiomethyl)-imidazole. Such compounds, particularly the 4-(2-aminoethylthiomethyl)-imidazoles, have found use as intermediates for preparing commercially important medicinal agents having histamine $H_2$-agonist activity. One indication of such activity is the inhibition of gastric acid secretion (see Black et al, Nature 1972, 236-385). An example of one of the end products made from such thioamines is cimetidine, N-cyano-N'-methyl-N''-[5-methyl-4-imidazolyl(methylthio)-ethyl]guanidine, see U.S. Pat. No. 3,950,333.

The thioamine used in one such process is prepared by reaction of cysteamine with the reaction product mixture produced by the electrochemical reduction of imidazole carboxylic esters, such as the reduction of lower alkyl 4-imidazolecarboxylates to give a mixture of the corresponding alcohol and lower alkyl ethers, see U.S. Pat. No. 4,055,573. This patent teaches a method for preparing 4-(hydroxymethyl)-imidazoles in mixture with their lower alkyl ethers by electrochemical reduction in concentrated sulfuric acid in concentrated solutions using standard electrochemical cells with yields up to 80%. Subsequent reaction of the mixed alcohol-alkyl ether with cysteamine hydrochloride produces the corresponding thioamine in about 60% yield. Several of the processes for production of 4-(hydroxymethyl)-imidazoles have the disadvantage of producing a diether of the desired compound which is a bis-(imidazolylmethyl)-ether hydrochloride. This bis-(imidazolylmethyl)-ether represented a yield loss of desired intermediate and an undesirable impurity requiring separation.

The conversion of this bis-(imidazolylmethyl)-ether hydrochloride to the corresponding 4-(hydroxymethyl)-imidazole by acid catalyzed ether cleavage was considered. Further, it was thought to be even more desirable if the bis-(imidazolylmethyl)-ether hydrochloride could be converted to the corresponding 4-(Ω-amino-alkylene-thiomethyl)-imidazole, i.e., the corresponding thioamine, directly. However, investigation of the chemical literature indicated that classical acid catalyzed ether cleavage required strong acid and produced at least one equivalent of the corresponding halide, sulfate or other acid anion salt. See Fieser et al, Organic Chemistry, 3rd Ed., Reinhold Publishing Co., New York, p. 137 (1956); Jaques et al, J. Chem. Soc. (London), 1964, pp. 2683-89; Daniels et al, J. Org. Chem., 1962, Vol. 27, pp. 4710-11; Patai, The Chemistry of the Ether Linkage, pp. 22-42, Interscience-Wiley, 1967. Further, the stability of the ether linkage to milder conditions and the use of amine salts was thought to be of insufficient strength to cleave the ether linkage and form the thioamine. See Burwell, The Cleavage of Ethers, Chem. Rev., Vol. 54, pp. 635-6 (1954).

THE INVENTION

It has now been found, however, that such bis-(imidazolylmethyl)-ether hydrochlorides are equivalent to 2 moles of a 4-(hydroxymethyl)-imidazole hydrochloride and can be reacted as such with a suitable amount of aminothiol, such as cysteamine hydrochloride, to prepare the corresponding thioamine. Alternatively, such bis-(imidazolylmethyl)-ether hydrochlorides can be reacted together with the 4-(hydroxymethyl)-imidazole hydrochloride to form the corresponding thioamines. Such finding provides a very advantageous process for the formation of desirable thioamine compounds.

Based on the above discovery, it is an object of this invention to convert bis-4-imidazolylmethyl ethers to the aforementioned corresponding thioamines in good yield. Another object of this invention is to convert mixtures of 4-(hydroxymethyl)-imidazole hydrochlorides and such bis-(imidazolylmethyl)-ether hydrochlorides to such thioamines. Another object of this invention is to simplify processes for producing thioamines by eliminating the need to separate, recycle and reconvert bis-ethers to 4-(hydroxymethyl)-imidazole hydrochlorides prior to formation of the corresponding thioamines. The foregoing and other objects of this invention are accomplished by a process for preparing a 4-(amino-alkylene-thiomethyl)-imidazole comprising reacting a bis-(imidazolylmethyl)-ether hydrochloride compound of formula

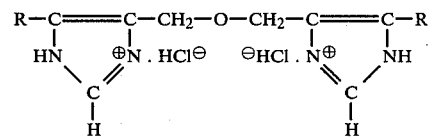

in which R is a lower alkyl group having from 1 to 4 carbon atoms with an amino thiol at temperatures sufficient to obtain said 4-(amino-alkylene-thiomethyl)-imidazole.

Another aspect of the present invention resides in the preferred embodiment of the above process further characterized in that the reaction of said amino thiol is carried out with a mixture of said compound and a 4-(hydroxymethyl)-imidazole hydrochloride to produce said 4-(amino-alkylene-thiomethyl)-imidazole.

The process of our invention employs as a starting material a compound of the formula given hereinabove. Such a compound is generally known as a bis-4-(5-alkyl)-imidazolyl methyl ether hydrochloride but for convenience will be referred to herein as a bis-(imidazolylmethyl)-ether hydrochloride. As indicated, the preferred starting material is a compound of the above given formula in which R is a lower alkyl group having from 1 to about 4 carbon atoms. Most preferred starting materials of this invention are compounds of the above given formula in which the lower alkyl group is methyl. The bis-(imidazolylmethyl)-ethers are generally produced during the process for production and recovery of a 4-(hydroxymethyl)-imidazole hydrochloride. Generally, such bis-(imidazolylmethyl)-ether hydrochlorides may be present in the mixture at about 2 to about 60 weight percent based on the 4-(hydroxymethyl)-imidazole hydrochloride. Alternately, the bis-(imidazolylmethyl)-ether hydrochlorides can be isolated from mixtures of 4-(hydroxymethyl)-imidazole hydrochlorides by recrystallization from isopropanol to give compositions containing 95 weight percent of the bis-(imidazolylmethyl)-ether hydrochlorides.

The bis-(imidazolylmethyl)-ether hydrochlorides or mixtures of bis-(imidazolylmethyl)-ether hydrochloride and 4-(hydroxymethyl)-imidazole hydrochloride are reacted with an aminothiol to produce thioamine intermediates of commercial significance. Aminothiols useful in the present process are amino-alkylene-thiols having an alkylene group, preferably a straight chain hydrocarbyl alkylene group, in which the amino group is at one end of the alkylene chain and the thiol group is at the other end of the alkylene chain. Preferably employed aminothiols are the terminal amino-alkylene-thiol, which may be generally termed $\Omega$-amino-alkylene-thiols, although the amino group can also be placed on an internal carbon atom of the alkylene chain. Of course, the use of a terminal amino-alkylene-thiol in the process of the present invention will produce the corresponding 4-($\Omega$-amino-alkylene-thiomethyl)-imidazole.

Preferably alkylene chains having from about 2 to about 4 carbon atoms and, most preferably, having 2 carbon atoms can be used in the aminothiol of this invention. Thus, preferred aminothiols are 2-aminoethanethiol, 3-aminopropanethiol, 4-aminobutanethiol and their isomers. Preferably, the aminothiol is employed as the hydrochloride salt. In general, it requires about 1 mole of aminothiol for each mole of imidazole equivalent. Thus, with the bis-(imidazolylmethyl)-ether hydrochlorides, 2 moles of aminothiol are required. When reacting in mixtures of 4-(hydroxymethyl)-imidazole and bis-(imidazolylmethyl)-ether, the equivalents of imidazole can be determined and a corresponding amount of aminothiol can be employed.

Although it is not required, the reaction can be facilitated by being carried out in a reaction medium having a boiling point which is not so high as to degrade the starting product but sufficiently high to give good reaction at reasonable times. Also, the reaction medium should be substantially inert to the reactants employed and products produced. Preferably, the reaction medium should be relatively inexpensive, readily available and not adversely affect the reaction or recovery equipment. In view of these considerations, a reaction medium having a boiling point at a temperature from about 75 to about 150° C. is preferred. Good reaction temperature control is obtained by conducting the process of our invention at the reflux temperature of the reaction medium. Particularly, it has been found that water is an acceptable reaction medium. Further, an aqueous carboxylic acid such as acetic acid has also been found to provide an advantageous reaction medium. More particularly, glacial acetic acid is a preferred reaction medium.

In general, the process of this invention involves addition of the reaction medium to the process vessel followed by addition of the aminothiol and bis-(imidazolylmethyl)-ether hydrochloride or mixture of bis-(imidazolylmethyl)-ether hydrochloride and 4-(hydroxymethyl)-imidazole hydrochloride. The reactor contents are then heated to a temperature sufficient to obtain reflux and for a period sufficient to obtain a substantial amount of the thioamine. In general, the reflux period can be from about 2 to about 10 hours. Times greater or lesser than these can be employed so long as the starting materials and thioamine reaction products are not adversely affected.

The process of the present invention can be more easily illustrated from consideration of the following examples which are non-limiting.

EXAMPLES 1–5

A mixture containing various amounts of 2-aminoethane thiol hydrochloride, 4-(hydroxymethyl)-5-methyl-imidazole hydrochloride and from 0 up to about 60 weight percent based on the total amount of imidazole of bis-[4-(5-methyl)-imidazolylmethyl]ether hydrochloride were placed in an agitated reactor fitted with a reflux condenser. Glacial acetic acid was used as the reaction medium. The reactor contents were heated to reflux and maintained at that temperature for 10 hours. Following this, the reaction mixture was cooled and the crystallized product filtered, washed with isopropanol and dried. The product was analyzed by NMR to be 5-methyl-4-(2-amino-ethyl-thiomethyl)imidazole. The product crystallizes as the dihydrochloride containing one mole of acetic acid. The conditions and results of these experiments are given in the following table:

| Example Number | PREPARATION OF THIOAMINE | | | | |
|---|---|---|---|---|---|
| | 1 | 2 | 3 | 4 | 5 |
| Imidazole Analysis, Wt. % by NMR | | | | | |
| Bis-4-(5-methyl)-imidazolyl methyl ether hydrochloride | None detected | 9.5 | 43 | 59.6 | 95+ |
| 5-Methyl-4-(hydroxymethyl)-imidazole hydrochloride | 98 | 83.5 | 57 | 26.6 | — |
| Impurities | None measured | 0.0 | — | 13.8 | — |
| Stoichiometry | | | | | |
| (1) Moles bis-4-(5-methyl)-imidazolyl ether hydrochloride | 0 | 0.0034 | 0.0114 | 0.0119 | 0.0158 |
| (2) Moles 4-(hydroxymethyl)-imidazole hydrochloride | 0.0924 | 0.0562 | 0.0284 | 0.0100 | 0 |
| (3) Mole equivalents imidazole[a] | 0.0924 | 0.0630 | 0.0512 | 0.0338 | 0.0316 |
| (4) Moles 2-aminoethane thiol hydrochloride | 0.0934 | 0.0670 | 0.0528 | 0.0378 | 0.0318 |
| (5) Amount of glacial acetic acid, ml | 93 | 60 | 50 | 35 | 27 |
| Conversion to Thioamine, % | 100 | 92.3 | 100 | 79.6 | 82 |

[a]Mole equivalents imidazole = [2 × (1)] + (2)

From the foregoing examples, it can be seen that the bis-ether converts in all respects to the thioamine equally as well as the 4-(hydroxymethyl)-imidazole. Isolated yields based on the 4-(hydroxymethyl)-imidazole content would otherwise be well in excess of 100% of theory which is impossible.

EXAMPLE 6

This example illustrates the conversion of bis-4-(5-methyl)-imidazolyl methyl ether hydrochloride to the corresponding thioamine in a reaction medium which does not contain acetic acid. A mixture of 1.4 grams (5.0 mmol) of bis-4-(5-methyl)-imidazolyl methyl ether hydrochloride and 1.1 grams (10.1 mmol) of 2-amino ethane thiol hydrochloride was heated in 10 ml of water in a 140° C. oil bath. The water evaporated in about 15 minutes and as the water evaporated an additional 30 mls of water in 10 ml increments was added during the reaction. A sample taken at the end of water evaporation the last time showed the reaction mixture to be 99% of the corresponding thioamine and 1% of the starting bis-imidazolyl ether.

EXAMPLE 7

In this example, the conversion of bis-4-(5-methyl)-imidazolyl methyl ether hydrochloride to the corresponding 4-(2-amino-alkylene-thiomethyl)-imidazole in the absence of a reaction medium is illustrated. A mixture of 4.04 grams of 4-(hydroxymethyl)-5-methyl-imidazole hydrochloride containing 2.2 weight percent of bis-4-(5-methyl)-imidazolyl ether hydrochloride was mixed with 3.12 grams of 2-amino ethane thiol hydrochloride. The solids were heated by an oil bath at a temperature of 140°-150° C. with stirring until they melted and the mixture became homogeneous after about 5 minutes. After continued heating and stirring for an additional 10 minutes a sample of the reaction melt analyzed by NMR showed 100% conversion to the 5-methyl-4-(2-aminoethyl-thiomethyl)-imidazole. Thus, all of the bis-imidazolylmethyl ether was converted to the corresponding 5-methyl-4-(2-aminoethyl-thiomethyl)-imidazole without the necessity for an aqueous or acid reaction medium.

In an attempt to verify the process of our invention, a comparative experiment using the procedure of Examples 1–5 was conducted in which 9.9 grams (50 mmoles) of benzyl ether, 5.7 grams (50 mmoles) of 2-amino ethane thiol hydrochloride and 50 milliliters of glacial acetic acid were heated to reflux under a nitrogen atmosphere. After refluxing for 17 hours, the reaction mixture was cooled and analyzed by NMR. No thioamine was detected. Only 1-2% of benzyl acetate was observed. Thus, as expected, the benzyl ether did not cleave in the presence of weak acid at the reflux temperature of acetic acid in the presence of cysteamine hydrochloride. The result of this experiment is what one skilled in the art would expect under the conditions employed. Thus, it is indeed surprising and unexpected to obtain the advantageous reaction of our process when a bis-(imidazolylmethyl)-ether hydrochloride is converted to the corresponding thioamine.

The process of the present invention, as particularly described in Examples 1–7 with 2-aminoethanethiol, can be similarly carried out using 3-aminopropanethiol and 4-aminobutanethiol to obtain the corresponding thioamines.

Having described the process of our invention, it is clear that various changes and modifications can be made which are within the scope of the invention. Therefore, it is desired to limit the invention only by the lawful scope of the following claims.

What is claimed is:

1. A process for preparing a 4-(amino-alkylene-thiomethyl)-imidazole consisting essentially of reacting a bis-(imidazolylmethyl)-ether hydrochloride of formula

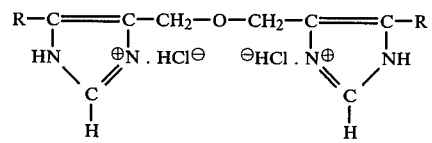

in which each R group is a lower alkyl group having from 1 to 4 carbon atoms with an amino alkylene thiol in which the alkylene group has from 2 to 4 carbon atoms, said reaction being carried out at a temperature from about 75° to 150° C. for a period sufficient to obtain said 4-(amino-alkylene-thiomethyl)-imidazole.

2. The process of claim 1 in which R is methyl.

3. The process of claim 1 in which said amino thiol is a terminal amino-alkylene-thiol.

4. The process of claim 1 in which said amino thiol is 2-aminoethanethiol hydrochloride.

5. The process of claim 1 further characterized in that said bis-(imidazolylmethyl)-ether hydrochloride and said amino thiol are contacted in a reaction medium, heated to reflux and maintained under reflux conditions for a period sufficient to obtain substantial quantities of said 4-(amino-alkylene-thiomethyl)-imidazole.

6. The process of claim 1 in which said reaction is carried out for a period of 8 to about 10 hours.

7. The process of claim 1 in which said reaction medium is acetic acid.

8. The process of claim 1 in which said reaction medium is glacial acetic acid.

9. The process of claim 1 further characterized in that the reaction of said amino thiol is carried out with a mixture of said bis-(imidazolylmethyl)-ether hydrochloride and a 4-(hydroxymethyl)-imidazole hydrochloride to produce said 4-(amino-alkylene-thiomethyl)-imidazole.

10. The process of claim 9 in which said mixture is composed of from 2 to about 60 weight percent of said bis-(imidazolylmethyl)-ether hydrochloride and from about 30 to about 98 weight percent of said 4-(hydroxymethyl)-imidazole hydrochloride.

* * * * *